US008126727B2

(12) United States Patent
Peterson (10) Patent No.: US 8,126,727 B2
(45) Date of Patent: Feb. 28, 2012

(54) SYSTEM AND METHOD FOR OBTAINING, MAINTAINING AND MAXIMIZING HEALTHCARE BENEFITS

(75) Inventor: Robert A. Peterson, Madison, WI (US)

(73) Assignee: My Coverage Plan Inc., Madison, WI (US)

( * ) Notice: Subject to any disclaimer, the term of this patent is extended or adjusted under 35 U.S.C. 154(b) by 894 days.

(21) Appl. No.: 11/832,288

(22) Filed: Aug. 1, 2007

(65) Prior Publication Data

US 2008/0033756 A1 Feb. 7, 2008

Related U.S. Application Data

(60) Provisional application No. 60/821,085, filed on Aug. 1, 2006.

(51) Int. Cl.
*G06Q 50/00* (2006.01)

(52) U.S. Cl. ............................................................ 705/2

(58) Field of Classification Search .................. 705/2, 4, 705/3; 364/401
See application file for complete search history.

(56) References Cited

U.S. PATENT DOCUMENTS

| | | | |
|---|---|---|---|
| 5,070,452 A | 12/1991 | Doyle | |
| 5,832,447 A | 11/1998 | Rieker | |
| 5,991,729 A | 11/1999 | Barry | |
| 6,012,035 A * | 1/2000 | Freeman et al. | 705/2 |
| 6,873,960 B1 | 3/2005 | Wood | |
| 6,879,959 B1 | 4/2005 | Chapman | |
| 2002/0010597 A1 | 1/2002 | Mayer | |
| 2002/0029157 A1 | 3/2002 | Marchosky | |
| 2002/0049617 A1 | 4/2002 | Lencki | |
| 2002/0069090 A1 | 6/2002 | De Grosz | |
| 2003/0009355 A1 | 1/2003 | Gupta | |
| 2003/0036926 A1 | 2/2003 | Starkey | |
| 2003/0046116 A1 | 3/2003 | Horowitz | |
| 2003/0139945 A1 | 7/2003 | Brown | |
| 2003/0160809 A1 | 8/2003 | Marion | |
| 2003/0191667 A1 | 10/2003 | Fitzgerald | |
| 2004/0039608 A1 | 2/2004 | Mazur | |
| 2004/0064343 A1 | 4/2004 | Korpman | |
| 2004/0093242 A1 | 5/2004 | Cadigan | |
| 2004/0117203 A1 | 6/2004 | Brand | |
| 2004/0128163 A1 | 7/2004 | Goodman | |
| 2004/0148203 A1 | 7/2004 | Whitaker | |
| 2004/0153337 A1 | 8/2004 | Cruze | |
| 2004/0186744 A1 | 9/2004 | Lux | |
| 2004/0186746 A1 | 9/2004 | Angst | |
| 2004/0210458 A1 | 10/2004 | Evans | |
| 2004/0220829 A1 | 11/2004 | Baharav | |

(Continued)

OTHER PUBLICATIONS

US Department of Labor Web Page (COBRA).*

(Continued)

*Primary Examiner* — Gerald J. O'Connor
*Assistant Examiner* — John Pauls
(74) *Attorney, Agent, or Firm* — Craig A. Fieschko, Esq.; DeWitt Ross & Stevens S.C.

(57) ABSTRACT

A system and method for obtaining, maintaining, and maximizing health care coverage benefits for individuals and families is provided. Patient data is applied to health care coverage program criteria and a patient specific coverage report is generated. Notification alerts are generated and provide a users change event notifications. Proximity alerts are generated and provided within the coverage report, identifying potential loss and gain of coverage benefits and eligibility.

26 Claims, 5 Drawing Sheets

U.S. PATENT DOCUMENTS

| | | |
|---|---|---|
| 2004/0230502 A1 | 11/2004 | Fiacco |
| 2005/0010446 A1 | 1/2005 | Lash |
| 2005/0015280 A1 | 1/2005 | Gabel |
| 2005/0055251 A1 | 3/2005 | Ashley |
| 2005/0060201 A1 | 3/2005 | Connely |
| 2005/0065818 A1 | 3/2005 | Brinkman |
| 2005/0102172 A1 | 5/2005 | Sirmans |
| 2005/0187797 A1 | 8/2005 | Johnson |
| 2005/0203781 A1 | 9/2005 | Wilson |
| 2005/0209893 A1 | 9/2005 | Nahra |
| 2005/0222867 A1 | 10/2005 | Underwood |
| 2005/0261944 A1 | 11/2005 | Rosenberger |
| 2005/0278196 A1 | 12/2005 | Potarazu |
| 2005/0288964 A1 | 12/2005 | Lutzen |
| 2005/0288968 A1 | 12/2005 | Collins |
| 2006/0143049 A1* | 6/2006 | Dean .............................. 705/3 |
| 2007/0038487 A1* | 2/2007 | McCarthy ....................... 705/4 |

OTHER PUBLICATIONS

Fulcher, J., "The use of patient biometrics in accessing electronic health records," International J of Healthcare Tech and Management, v. 6(1):20-31, 2004.

Henrard, S., "Preliminary instrumentation for the efficient use of web-based electronic health records," IEEE Symposium on Computer Based Medical Systems, ISSN 1063-7125, v. 17:10-14, 2004.

National Assoc of Health Underwriters (NAHU), "Welcome to the health care coverage options database," 2 pgs. URL: http://www.nahu.org/consumer/healthcare/index.cfm, printed on Jan. 10, 2008.

O'Bleness, E., "From electronic document management to EHR [electronic health records]," Health Management Technology, v. 26(1):54-5, Jan. 2005.

Schoen, C., et al, "Insured but not protected: How many adults are underinsured?" Jun. 13, 2005 (4 pgs). Source: http://www.commonwealthfund.org/publications/publications_show.htm?doc_id=280812.

Wimalasiri, J. S., et al, "Security of electronic health records based on Web services," Conference: Proceedings of 7th International Workshop on Enterprise Networking and Computing in Healthcare Industry. HEALTHCOM 2005 (IEEE Cat. No. 05EX1016) p. 91-95, Jun. 23-25, 2005.

* cited by examiner

SYSTEM AND METHOD FOR OBTAINING, MAINTAINING AND MAXIMIZING HEALTHCARE BENEFITS

CROSS REFERENCE TO RELATED APPLICATION

This application claims priority to provisional U.S. Patent Application Ser. No. 60/821,085, filed Aug. 1, 2006.

FIELD OF THE INVENTION

This invention generally relates to the collection and analysis of data. More particularly, the present invention relates to the collection and analysis of data for obtaining, maintaining, and maximizing healthcare benefits.

BACKGROUND OF THE INVENTION

According to the Census Bureau figures, in 2004 approximately 15.7% of the U.S. population lacked any form of health care coverage, including either public or private. These 45,800,000 Americans are referred to as the uninsured. In 2002 the number was approximately 15.3% or 43,600,000 Americans. Of the population that currently has some form of health care coverage, it is estimated that approximately 16 million American adults are underinsured. This poses a significant risk to individuals and the health care system because an underinsured individual does not have adequate protection against severe health care expenses.

Due to the continued need for medical treatment, uninsured and underinsured individuals are a significant burden to the health care system. The growth in the number of uninsured and underinsured Americans will undoubtedly continue into the foreseeable future. Despite the size of this population, uninsured and underinsured individuals remain a costly entity to the health care system.

Those lacking health care coverage face the health care system as an unknown. Even more pressing is the tremendous burden and cost that is placed upon the health care system for providing health care to uninsured and underinsured individuals. Those who gain and lose health care coverage present a problem that can often be solved, as those who are insured are more likely to be able to maintain at least a minimal level of coverage. Maintaining coverage for even a small fraction of those who have transitioned from covered to uninsured can save the health care system a significant amount of money. Additionally, maximizing health care coverage for the underinsured has significant potential for relieving financial and social burdens upon the health care system.

These realities have consequences in terms of escalating costs, inefficiencies, and inequities. Public and private efforts have focused on specific problem areas, but these efforts have not specifically addressed the incidence of identifying available health care coverage and actually increasing health care coverage for uninsured individuals and families. Increasing health care coverage has the direct effect of decreasing the level of uninsured and underinsured people, which in turn has a significant impact upon the entire system. Furthermore existing systems do not provide a means for reducing the number of Americans who lose coverage by providing a means for maintaining and maximizing medical benefits coverage.

SUMMARY OF THE INVENTION

In at least one embodiment of the invention, the system includes a relational database, the database having access to health care benefits program data, the program data includes criteria for participation in the program. The system also includes a memory storage device configured for storage of health care related data. A processor for controlling the system is included, wherein the processor applies the health care criteria to the health care related data and generates eligibility statistics. The processor also generates a user notification based upon occurrence of a change event.

In another embodiment of the invention a method for maintaining and maximizing health care coverage includes the steps of entering patient data into a memory storage device and based upon the patient data, applying benefits coverage criteria to the patient data. The method also includes identifying additional benefits programs, wherein the benefits programs provide health care coverage benefits to the patient, and entering updated patient data into a memory storage device, wherein the updated patient data is dynamically applied to the criteria. The method also includes the steps of dynamically providing a benefits program roadmap, wherein the roadmap prompts the user to fulfill healthcare benefits criteria, and providing a change event status notification, the notification including potential loss of benefits data and potential new benefits opportunities.

In yet another embodiment of the invention a method for providing a patient-specific benefits coverage report includes the steps of inputting patient-specific data into a memory storage device and inputting benefits program criteria into a relational database. The method includes the steps of applying the user-specific data to the program criteria and generating a patient-specific benefits coverage report, where the report has a benefits section, a benefits maintenance roadmap and benefits program proximity alert section, the benefits section provides current available benefits and the roadmap providing user-specific program requirements. The proximity alert section provides potential benefits program eligibility based upon patient-specific data and key program requirements.

BRIEF DESCRIPTION OF THE DRAWINGS

The drawings illustrate one mode presently contemplated for carrying out the invention.

In the drawings.

DETAILED DESCRIPTION OF THE PREFERRED EMBODIMENT

Figure 1:
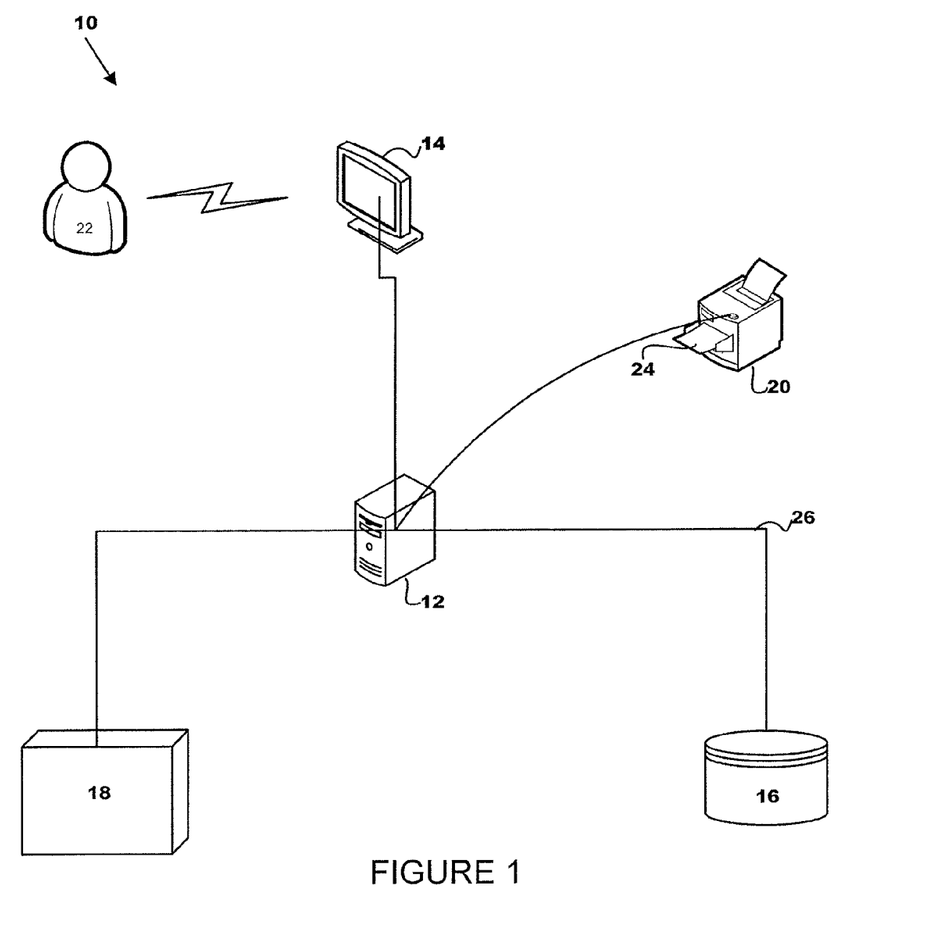
FIG. 1 is a block diagram illustrating an exemplary system, in accordance with at least one embodiment of the present invention.

Referring to FIG. 1, an exemplary embodiment of the health care benefits system 10 is provided. The system 10 comprises a central processing unit (CPU) 12, a graphical user interface (GUI) 14, a relational database 16, a memory storage system 18, and a printing device 20. The CPU 12 is a computer that controls system 10 processes. The system 10 processes include GUI 14 control and display for use by a user 22, memory storage and retrieval, database 16 access, and report 24 generation printing and displaying. The GUI 14, database 16, memory device 18, and printer 20 are connected to the CPU 12 via connectors 26. Connectors 26 provide a means for transmitting data between the respective devices. The connectors 26 may be physical wires or wireless communication signals. Memory 18 may alternatively be located separate from the CPU 12 and accessible through a web server (not shown).

GUI 14 provides an interface between the user 22 and the system 10. Health care coverage reports 24 are available for viewing by the user 22 through use of the GUI 14. The user 22 can be a system administrator who inputs data into the system through the GUI 14. A patient can also access the system 10 through the GUI 14. A keyboard (not shown) or another peripheral device known in the art can be used as a means to interface with the controller 12. Such an interface can include the input of patient data and medical coverage program criteria. Patient data and program criteria, as well as other data, is also input to the system through automatic data downloads and controlled system updates.

Generally healthcare coverage programs are varied in source and administration. Program criteria and eligibility requirements frequently change. Program updates are dynamically input through an input/output (I/O) device (not shown). Program updates can be in the form of a patch or another comparable executable with the purpose of changing the system configurations. Data downloads are provided through the I/O device and saved within system memory 18. Additionally, data update means known in the art are contemplated. The system 10 can be configured to allow a system administrator to verify the data downloads prior to implementing any changes to patient data or program criteria.

Data is stored within a memory storage device internal (not shown) or external 18 to the database 16. Patient data is provided by the patient and saved on the memory storage device 18. Data files storing case management codes are accessed by the database 16 for organizing patient and medical coverage program information. Case management codes include referral codes, outcome codes, trigger codes, complications codes, service provider codes, service request codes, problem codes, and funding codes. Condition code files are accessible by the database, stored in memory 18, and are used for organizing patient data. By example, condition codes can include the following subjects: marital status, family structure, ethnicity, language and insurance status. The controller 12 organizes the patient data and associates the data with codes as a means for organizing the data.

Condition and case management codes provide the user 22 with the ability to generate specifically designed, customized, and general reports for patient and administrative use. By example, a patient usage report can be generated to analyze the cost benefit for health care providers. The report 15 used for data analysis which includes benefits usage, user demographics, patient income and ages. Based upon the data analysis, the system 10 can identify patients able to obtain or maximize coverage. Coverage is often higher for children and pregnant women, to insure good prenatal care and high birth rates. Uninsured and underinsured are therefore able to obtain coverage and maximize coverage through use of the information provided by the system 10 reports.

An advocate 22 is a health care worker who assists the patient in obtaining and maintaining health care coverage for the patient. Advocates 22 are also system users, and depending upon the system administrator, advocates have administrative or full access to multiple patient files. Patients typically do not have administrative access to the system 10. Based upon the system administrator system 10 access is varied. Patients have the lowest level of system access while the system administrators have full access. Based upon the access level provided enhanced content can be available. By example, system administrators and advocates have access to educational tutorials designed to provide information relating to using the system for a patients benefit (See FIG. 5). Tutorials also provide information for the health care benefits programs. The tutorials offer an explanation of scenarios for enhancing care and program eligibility. Alternatively, tutorials can be provided that inform the advocate of new programs and significant changes or the process of obtaining coverage.

Figure 2:
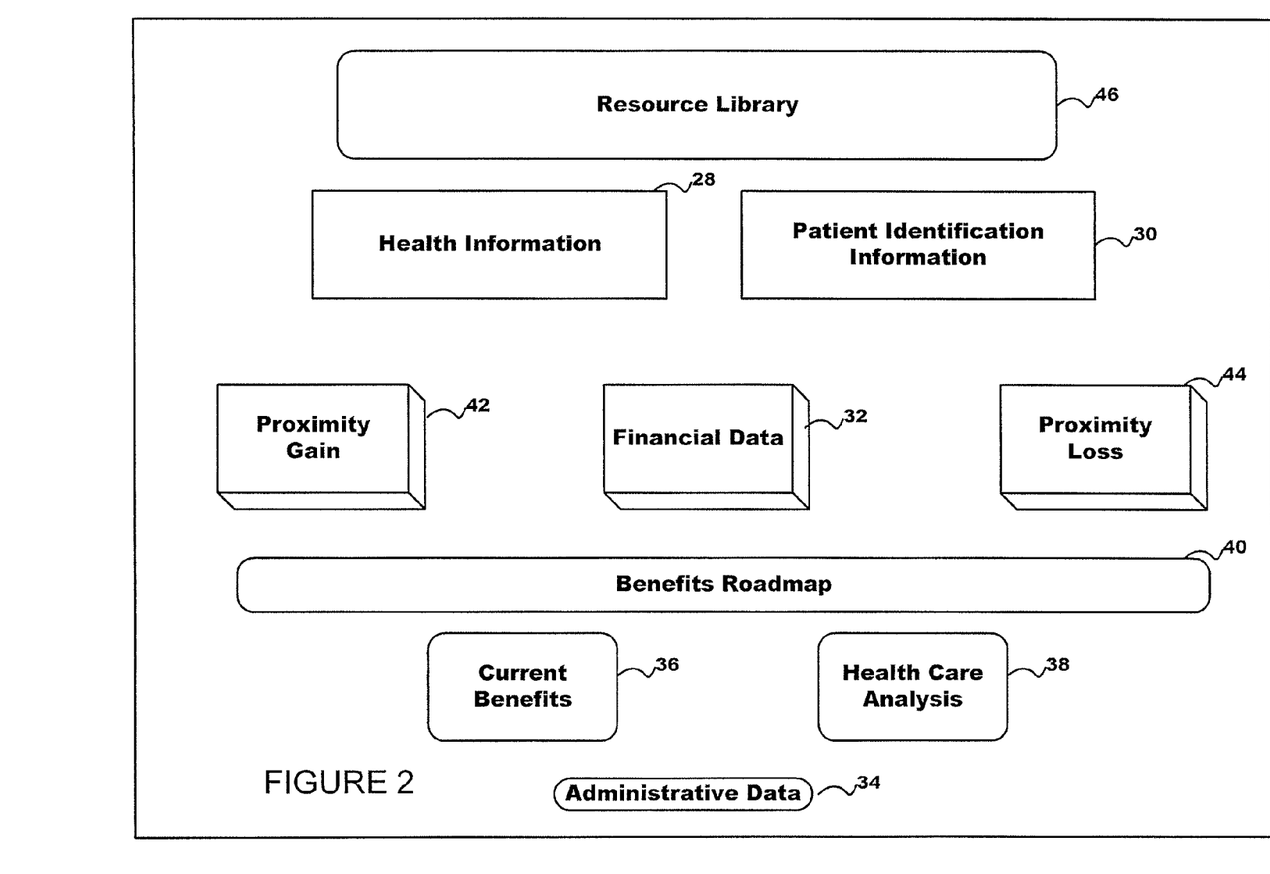
FIG. 2 is a block diagram illustrating an exemplary coverage report, in accordance with at least one embodiment of the present invention.

Referring to FIG. 2, an exemplary health care coverage report 24 is provided. The report 24 contains a plurality of sections that convey information to a patient 22 or health care case worker 22. The report 24 contains a health information section 28, a patient identification section 30, a patient financial data section 32, an administrative data section 34, a benefits section 36, a health care analysis section 38, a benefits and a health care maintenance roadmap 40. The report 24 is accessible by the user 22 through the graphical user interface 14. Alternatively, the report can be formatted for printing, via printer 20, in hard copy format. The hard copy format consists of multiple pages, typically a single page for each of the sections. Alternatively, the report can be formatted into a single summary page followed by multiple section pages.

The health information section 28 includes a summary of the patient's physical and mental health. Based upon user selected variables the system 10 generates a priority schema for health information. Information that is more pertinent to obtaining, maintaining and maximizing health care coverage is provided within this section. Alternatively, the user can access hyperlinked documents containing available patient medical records. Patient selectable rules provide health information within the report 24 that is most important to the user 22. Alternatively, the information section 28 includes detailed administrative information for use by a health care advocate 22.

The report 24 also includes a patient identification section 30, as patient-provided data is used by the database 16 to uniquely identify each patient. By example, the following types of information can be provided within section 30: patient name, social security number, patient address, patient phone and data numbers, and email address. Alternatively, a unique patient identifier code can be generated by the controller 12 and used as a primary key within the database 16 schema. The identifier code is unique to each user 22 and can be used in conjunction with or separate from the patient's social security number.

The patient financial data section 32 displays information that includes the following: income, federal poverty level (FPL) analysis, patient debt load, patient asset value, source of patient income, necessary treatment cost assessment, and treatment cost assessment. Financial data is often one of the criteria for obtaining, maintaining and maximizing health care coverage. Healthcare coverage programs, such as the Katie Becket Program, require that a household or patient's income not exceed a defined level. In order to be eligible for the Katie Becket Program the patient's family income must be less than 185% of the FPL. A patient is not considered for a program if they do not meet the criteria. However, a patient is eligible for the Katie Becket Program if their income is greater than 185% of FPL and qualifying debts reduce the income below this level. By providing the patient and advocate with proximity eligibility alerts and corresponding information the patient has a greater ability to obtain and maintain benefits coverage.

Advocates and administrative personnel have full access to the system, and therefore based upon selectable rules can include various types of information within section 32. By example, most patients 22 do not wish to have their sensitive information printed on the report 24. In order to prevent the patient from being completely forthright with their data, the system 10 allows the patient to inform the advocate of sensitive information to be included and excluded within the report 24, while maintaining the information within system memory 18.

An Administrative data section 34 is provided primarily for advocate use. Information including date of enrollment, residency issues, report identifier, confidentiality waiver information, system diagnostics, eligibility analysis, and patient referral identifiers are included within this section.

A current benefits information section 36 provides the patient's current health care coverage benefits. Medical or health-related programs utilized by the patient and the specifics of the coverage are included within this section 36. Information available within this section 36 is selectable by the user 22. By default, all available information regarding current benefits is listed, or summarized within this section 36. Though the system 10 is not limited to certain types of patients, those using the system 10 often have limited availability to common health insurance carriers. Patients that do not receive current benefits will have an empty section 36.

The health care analysis section 38 includes patient medical data and data pertinent to health care coverage programs. An advocate 22 or system administrator can input information into this section 38 and the patient typically has read access, but does not have write access to this data section 38. The section 38 includes advocate 22 entered comments and background information that is pertinent to obtaining, maintaining and maximizing health care coverage. By example, current and historic familial medical data, as well as familial medical debt loads, when available, are included within this section 38.

A health care coverage benefits roadmap section 40 includes information specific to current and future medical coverage program requirements. This section 40 provides automatic notifications of future events that can affect the maintenance of health care benefits coverage. By example, seasonal employees often have specified dates of employment which can change their eligibility for health care benefits programs. The system 10 prompts the user to provide patient data. Certain change events can be identified, such as a birthdates, which can affect the eligibility for certain programs not only for the patient but also for the patient's family. By example, program criteria can require patient submissions at set intervals or an annual re-certification process necessary to maintain coverage. For the purposes of this disclosure a change event is defined as a change in patient data, a benefits program criteria, or the existence of a benefits program that can, or as the potential to, change the eligibility for obtaining, maintaining or maximizing healthcare benefits coverage for a user 22.

In an alternative embodiment, proximity alert sections 42, 44 are provided as part of the report 24. Proximity loss alert section 44 provides information regarding potential or actual loss of benefits currently received by the patient that may occur in the future. The patient data is automatically applied against any currently enrolled programs. In the event that a patient's data has changed or is going to change, a proximity alert is generated and uploaded from the controller 12 into the report 24. Patient data such as age or actual future changes in program criteria can cause a loss alert to be generated. A system administrator sets the frequency for which a process is generated and executed for accomplishing this task, which can range from daily to weekly. Subsequent to the execution of the loss alert process is an analysis process. If the results from the loss alert process does not meet a threshold value, or if there is no potential loss, then a loss alert is not generated. Therefore, a change in criteria or patient data does not necessitate the generation of a loss alert, it can be generated when the criteria change is sufficient to generate a potential loss.

The proximity gain alert section 42 of the report 24 provides potential new programs available for the patient. A gain alert process is automatically generated and executed by the system 10. A system administrator determines the frequency and time for executing the gain alert process, much like the loss alert process. After executing the gain alert process the controller 12 executes an analysis process, which compares the results of the gain alert process to administrator defined rules. If the results from a gain alert process does not meet a threshold value defined by the rules, or if there is no potential gain as defined by the rules, then a gain alert is not generated. Provided with the proximity gain alert is a resource hyperlink, for GUI viewable versions of the report, which directs the user to access the potential coverage gain. In most cases, a new medical coverage program is now available based upon a patient data update, program criteria change, or a new program entirely. Program application materials are automatically provided to the user as part of the gain alert section 42.

Criteria that is imported into the relational database is specific and unique to the available healthcare coverage programs. At any given time there are dozens of health care coverage programs having required eligibility criteria. The required eligibility criteria are contained within the database structure, and when criteria are met the system provides an indication of high probability that a patient is eligible to receive the specific program's benefits and provides an application for submission to the administering entity.

In an alternative embodiment, a resource library section 46 is provided to the web browser based report. The resource library section provides hyperlinks to a variety of health care coverage resources. Resources can include insurance and program websites, Medicare information, strategies for obtaining, maintaining and maximizing health care benefits coverage, and informational user guides.

In yet another alternative embodiment, a benefits coverage record section (not shown) is provided to the patient on the report 24. The coverage record includes a historical record of health care benefits for the patient. The record can also include familial benefits records for families whose medical coverage may be linked. Benefits levels are also be provided, which indicate the time and level of coverage. The coverage record provides valuable information to patients seeking coverage as well as those attempting to maintain and maximize coverage. Various programs look at past benefits for eligibility of future benefits. By example, pre-existing conditions can be excluded and patients can be ineligible for programs based upon passing threshold coverage limits. Alternatively, the coverage record is merged with the benefits roadmap in the form of a hyperlinked timeline. The GUI 14 viewable format provides past medical data through hyperlinked documents saved in memory 18.

Figure 3:
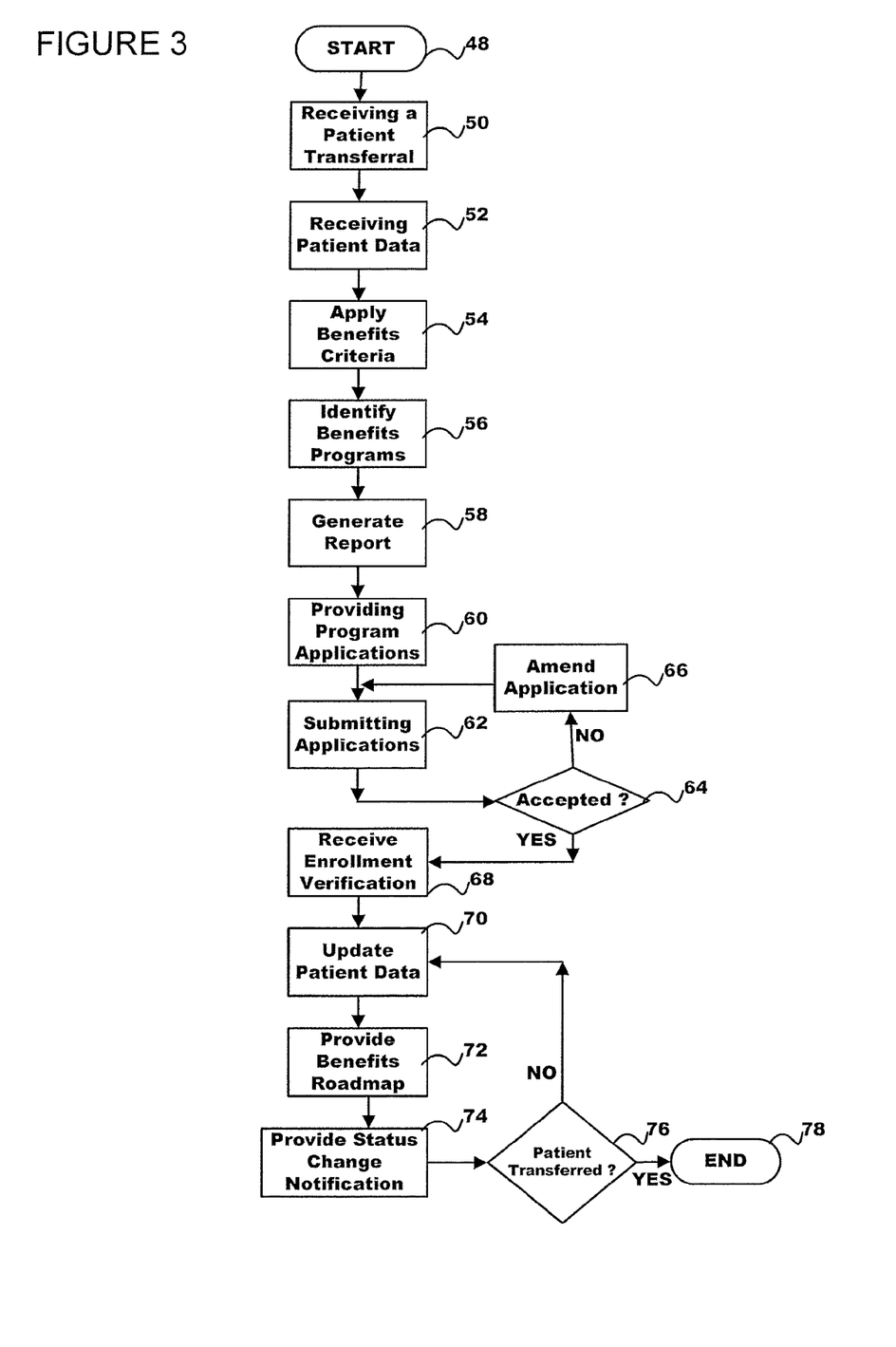
FIG. 3 is a flow diagram illustrating an exemplary method for obtaining and maintaining health care coverage, in accordance with at least one embodiment of the present invention.

Referring to FIG. 3, steps for a method of obtaining, maintaining and maximizing health care coverage are provided. The system 10 is initialized at step 48, and a patient transferal is received at step 50. Patient data is received at step 52. The system 10 can be incorporated within a health care system and transferals can be received from alternate health care systems. Patient data can be transferred from one health care system to the next, provided that the data is in comparable format or can be re-formatted for input into the system 10. The patient can provide the data to an advocate 22 or system administrator, and the data is manually entered.

After the patient data is archived 52 within memory 18 the archived benefits criteria are applied to patient data at step 54. Potential benefits programs are identified at step 56. Programs with high and medium probability are identified. The identified benefits programs are archived and a medical coverage report is generated at step 58. The report 24 provides the patient with prospective sources for medical benefits coverage. Programs defined as having a high probability of success are those for which the patient's data meets or exceeds approximately 90% of the archived criteria for the program. A medium priority program is defined as a program for which the patient's archived data meets or exceeds about 70% of the archived program criteria. Alternatively, the high and medium programs can be generated for patient data to program criteria thresholds in a range of about 80% to 100% and about 60% to 80% respectively. The percentage match of patient data to program criteria is calculated for each criteria separately and if the average of the combined percentages is within the defined range a higher medium probability match is identified. Alternative statistical methods known in the art are contemplated for calculating the percentage.

High probability medical benefits program applications are provided to the user 22 at step 60. Program applications can be provided in web-based or hard copy form. The patient reviews the application and submits the application at step 62. Prior to submitting the application the patient can confer with an advocate or access the resource library section 46 for assistance in filling out the application. If the application is not accepted at step 64 the patient must decide whether to pursue the application. If the patient pursues the application it is amended at step 66 and then submitted at step 62. Once the application is accepted 64 the patient receives an enrollment verification at step 68. The verification step may occur once the patient realizes that the program benefits are received. In an alternative embodiment, medium probability medical benefits program applications are provided to the user at step 60 in addition to high probability programs.

The patient data is updated at step 70, which increases the accuracy of eligibility determinations. A medical benefits roadmap is generated and provided to the patient at step 72. The report can alternatively be generated and provided to the patient at predetermined or customized time frames.

A change event triggers the system to apply the patient data to the program criteria. In the event of an actual or potential status change the system 10 will generate a change of status notification at step 74. The notice is provided to the patient and provides notice to a patient that a potential or actual loss of coverage is possible. The notification protocols are set to provide notice to the patient in a relatively short period of time from the change event.

In the event that the patient is transferred at step 76 the patient specific program terminates at step 78. If the patient is not transferred at step 76, then the system 10 reverts the patient program to step 70.

Figure 4:
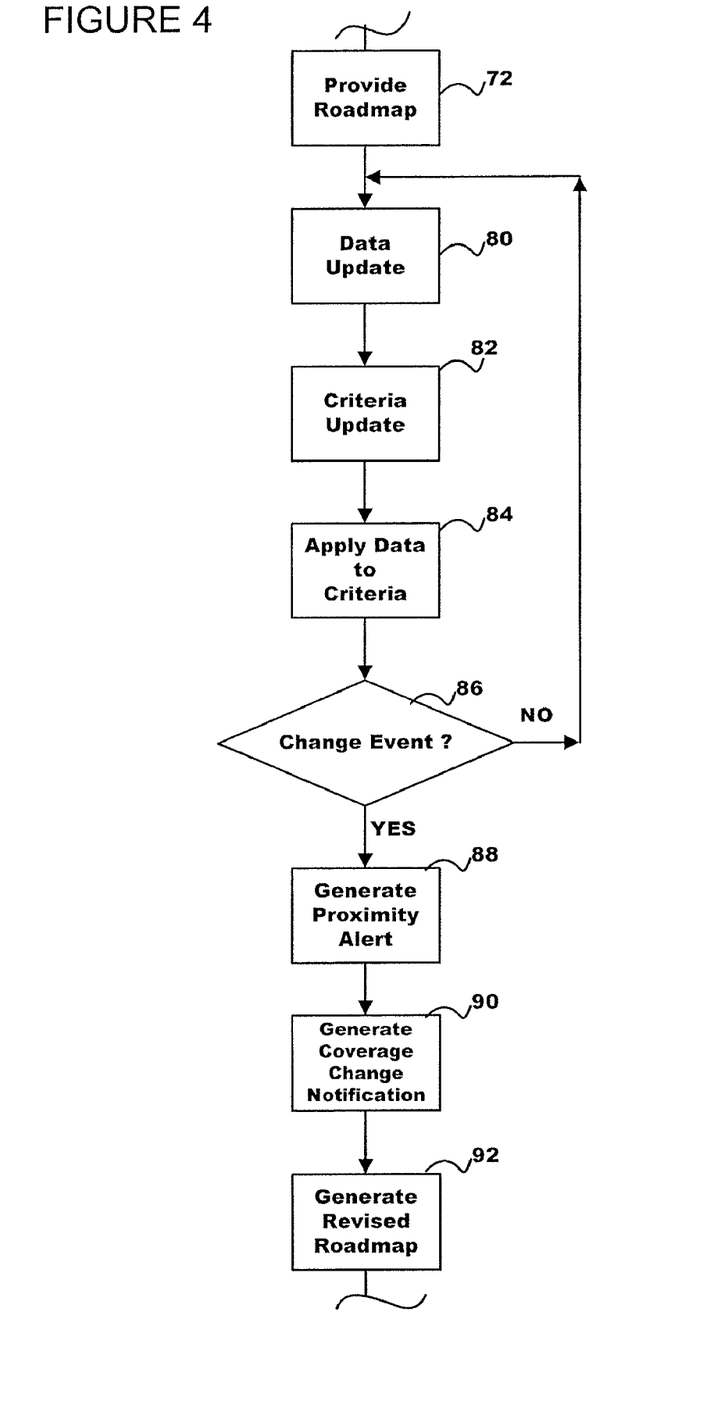
FIG. 4 is a flow diagram illustrating an exemplary health care report, in accordance with at least one embodiment of the present invention.

Now referring to FIG. 4, patient data is periodically updated by the system 10 and need not be limited by particular steps in the process for obtaining, maintaining and maximizing medical benefits. In an alternative embodiment, patient data is updated following the generation of a benefit coverage roadmap 72. Program criteria are updated at step 82. Alternatively, the program criteria and patient data can be updated simultaneously, or the program criteria are updated prior to the patient data update. The patient data is applied to the program criteria at step 84. If a change event occurs at step 86 then a proximity alert is generated at step 88. The proximity alert indicates a potential loss of coverage. Alternatively, a proximity alert indicating eligibility for a new health care benefits program. A coverage change notification is generated at step 90. The notice provides the user of an actual change of status that has or will occur in the future. Following the generation of the coverage change notification 90 the patient's data is applied to the criteria and a revised roadmap is generated at step 92.

Maintenance of health care coverage is extremely important, as it is easier to maintain benefits than it is to obtain them. However, the criteria that allowed benefits may change after coverage is obtained. In order to fully maximize a patient's coverage it is important to receive notices of potential loss of coverage, notices for meeting the criteria for different programs, and proximity alerts for identifying what programs can be available at the occurrence of a change event. Email notifications, letter notifications, and telephone prompts for the patient's advocate are a few ways that can be utilized when generating a change event notice and potential loss of coverage. Proximity alerts can also be generated. A proximity alert can be generated for one of two scenarios. An alert can provide an indication of potential loss of coverage or a potential gain in coverage.

Health care change events often alter the current eligibility and future maintenance of health care benefits. Change events may occur either as patient data changes or as the criteria for programs change. Change events include the transition beyond a program defined age threshold. By example, children who turn 18 may no longer be eligible to receive certain benefits, since the program requires the patient to be less than 18 years old. A patient's level of care may also effect eligibility for benefits, and can be considered a change event. Dependent upon the specific program, the magnitude of the change can effect whether it is determined to be a change event. The length of time since the patient was last insured can also be a change event. Moving, changing jobs, promotion/demotion, and the birth/death of a child/spouse can also be a change event. Programs have varying criteria and therefore no two programs are identical. Additionally, moving across state lines can also affect the eligibility for benefits. Change events are defined by the system administrator and are dependant upon the criteria for each coverage program.

In order to maximize a patient's current and future benefits it is crucial that the patient and advocate are provided notice of change events and the potential effect upon eligibility. An alternative notification is generated for requesting the update of a patient's data. Automatic letters or emails are generated to prompt the patient to provide correct and updated information. Collecting correct data from the patient is critical for obtaining, maintaining, and maximizing benefits coverage for the patient. Once a patient receives the notification she is directed to a secure login for the system 10 server, Through the GUI 14 a patient is able to provide any changes, additions or deletions to the pre-existing patient data. Subsequent to patient data changes a report process is executed. Alerts or notices are generated based upon the report process results.

By example, the Katie Becket Program provides Medicaid coverage for children with certain long-term disabilities. In order to be eligible for the program there are specific criteria that must be met. By example, the patient must be under a certain age (i.e. 19 years of age), and living at home while needing a level of care that is typically provided in a hospital or nursing facility. Additionally, the patient can not exceed a certain income or assets, which can vary depending upon when benefits are sought.

Another benefits program, by example, includes the Healthy Start Program, which provides Medicaid coverage for pregnant women, infants and children under the age of six (6). In order to be eligible for the program the patient's family income must be less than 185% of the federal poverty level. Due to relatively frequent changes in the federal poverty level the criteria programmed into the database must be reset in order to provide an accurate indication of eligibility.

Figure 5:
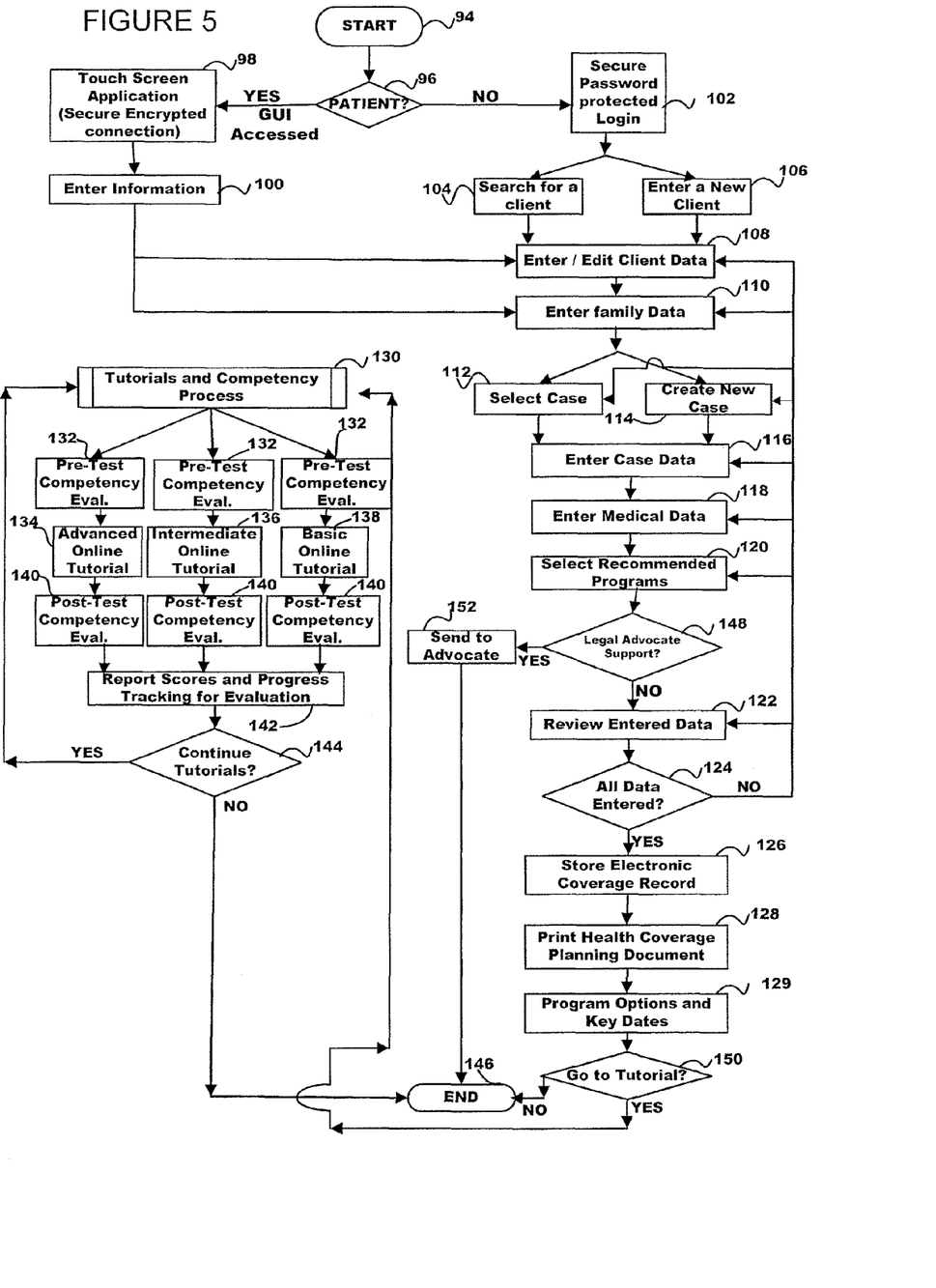
FIG. 5 is a flow diagram illustrating an exemplary method for obtaining, maintaining, and/or maximizing health care coverage, in accordance with at least one embodiment of the present invention.

Referring to FIG. 5, an alternative embodiment of the invention is described. The system 10 is initiated at step 94. If the user 22 is identified as a patient at step 96, the patient accesses the system 10 through a GUI at step 98. The GUI enables secure encrypted access to the system 10. Once the patient has gained access to the system 10, patient data is entered at step 100. If the user 22 is not identified as a patient at step 96, such as a medical provider, the system 10 requires secure login through a GUI at step 102. Secure login can be accomplished through various implementations, including passwords, biometrics and other security measures known in the art. Users can log out of the system 10 at any time after step 102. The medical provider is given the option to either search for a client at step 104, or enter a new client at step 106. Patient information is entered or edited at step 108 and patient familial information is entered at step 110. In an alternative embodiment, steps 108 and 110 are reversed. The user selects an existing patient case at step 112, or creates a new patient case at step 114. Once a case is selected or created, case information is entered at step 116. Medical information is entered at step 118. Regardless of the chosen path the system 10 can auto-populate various data fields based upon the patient information. Patient information can be entered by the patient, a medical provider, or some other individual such as a system administrator, by example. The patient case specific data is stored in a memory device 18 and accessed by the relational database. The patient data is based upon the patient's circumstances, and medical coverage programs are provided at step 120. The user reviews the data at step 122, and determines if all the patient data has been entered at step 124. If more data needs to be entered, or a new case is selected/created, then steps 108 through 118 can be repeated. In the event that all data has been entered, the patient electronic coverage record is sent to system memory at step 126. The user can then print off a copy of the report at step 128. For each eligible program a set of options and key dates are provided at step 129. Alternatively, the user accesses the tutorial 130 after step 120 or at any time while logged on to the system 10.

The system 10 provides tutorials and competency tools to the user at step 130. A competency pre-test is executed by the user at step 132. Dependent upon the results of the competency test, an advanced tutorial 134, intermediate tutorial 136, or basic tutorial 138 is provided to the user. After the tutorial is executed 134, 136, 138, a post-tutorial competency evaluation is provided at step 140. Scores and progress of the evaluations are plotted and evaluated at step 142. At step 144 the user decides whether to continue the tutorial and competency evaluation. If so, step 130 is repeated. Alternatively at step 144 the process is terminated at 146. Additionally, the user can send a legal advocate program information at step 148. By combining program tutorials, program options, and important program dates the consumers and health care providers are able to obtain, maintain, and/or maximize health care benefits for the consumers. This is especially the case for consumers not able to obtain conventional health care benefits. After step 129 the user can choose to access the tutorials at step 150, otherwise terminate at step 152.

The methodology as described in FIG. 5 is but one alternative embodiment of the invention that provides both a financial resource tool for health care providers and health care consumers, as well as a health care decision support system for consumers. Eligibility for a broad range of public and private health care benefits programs is achieved after step 120. The report generated can include details for both past and present program eligibilities. Furthermore, the report includes future eligibilities dependent upon predicted or potential changes in certain consumer variables. By example, a change event including age or seasonal employment termination can be predicted and change the eligibility of the consumer.

Various embodiments of the present invention are implemented through Internet browsers and easily accessible to consumers and health care providers alike. Alternatively, embodiments of the present invention are available through hospital kiosks and/or hospital network system terminals. Hospital kiosks provide a easy and straight forward GUI for consumers to enter data and access health records for the purpose of obtaining, maintaining and maximizing health care benefits coverage. Stand alone kiosks can be placed at various locales within the hospital and provide easy access for consumers. By example, kiosks can be placed close to an emergency room or a surgical waiting area. As relatives and guardians are present due to the illness of a related consumer, data can be entered and health care program eligibilities can be obtained for the consumer. This is especially valuable due to the consumers potential inability to access the system 10 and the preoccupation with ongoing health care issues. Furthermore, embodiments of the present invention generate health benefits eligibility reports (See step 128) that delineate individual health care coverage source history, recommend future health care financing options, and detail the effect of variable condition changes on benefits eligibility. By providing such a individually tailored health care financing roadmap, health care consumers are better able to make informed health care related decisions and maximize continuity of coverage.

In yet another alternative embodiment, the system 10 provides health care coverage options for consumers in each of the United States. Program eligibilities are available for each of the United States, including territories controlled by the United States. Eligibility for health care benefits programs are provided for the State of residence. However, a common change event is moving from one region to another. By moving, the consumer can either lose or gain eligibility for various private and public health care benefits programs. Furthermore, access to multi-region program eligibility ensures that health care provider networks can work with consumers over an extended geographic area. In at least one embodiment of the present invention dynamic drop down menus are available for the GUI to access different State or territory program variables.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A method for obtaining and maintaining patient health care benefits comprising the following steps:
   a. receiving patient data in a computer, the patient data relating to a patient and including demographic data, health data and financial data;
   b. based upon the patient data, applying health care benefits program coverage criteria for one or more health care benefits programs to the patient data within the computer, wherein the health care benefits program coverage criteria include enrollment eligibility conditions for each health care benefit program;
   c. within the computer, identifying:
      (1) any health care benefits programs wherein the patient meets all of the health care benefits program coverage criteria for each of the health care benefits programs, thereby identifying the health care benefits programs for which the patient is currently eligible for enrollment;
      (2) any health care benefits programs wherein the patient does not meet all of the health care benefits program coverage criteria for the health care benefits programs, but meets over at least 70% of the health care benefits program coverage criteria for the health care benefits programs, thereby identifying the health care benefits programs for which the patient is almost eligible for enrollment;
   d. for any identified health care benefits programs for which the patient is currently eligible for enrollment:
      (1) providing a benefits program enrollment application;
      (2) submitting the benefits program enrollment application;
      (3) receiving benefits program enrollment verification;
   e. for any identified health care benefits programs for which the patient is almost eligible for enrollment, identifying the health care benefits program coverage criteria that must be met by the patient to attain eligibility for enrollment;
   f. obtaining updated patient data;
   g. after obtaining updated patient data, dynamically providing a report identifying:
      (1) any health care benefits programs for which the patient is currently eligible for enrollment, and
      (2) any health care benefits programs for which the patient is almost eligible for enrollment, and the health care benefits program coverage criteria that must be met by the patient to attain eligibility for enrollment;
   h. providing a change event status notification, the notification identifying an actual or potential change event that alters benefits coverage based upon the patient data and health care benefits program coverage criteria.

2. The method according to claim 1 wherein identifying health care benefits programs includes:
   a. calculating a probability of receiving enrollment verification;
   b. reporting to the patient:
      (1) a first health care benefits program as having the greatest probability of receiving enrollment verification, and
      (2) a second health care benefits program as having a lower probability of receiving enrollment verification than the first health care benefits program,
   wherein a third health care benefits program having a lower probability of receiving enrollment verification than both of the first and second health care benefits programs is also identified within the computer.

3. The method according to claim 1 wherein the change of event status notification provides a user with eligibility for enrollment and health care benefits program maintenance information, whereby the notification reduces the likelihood that the patient will become uninsured.

4. The method of claim 1 further comprising the following steps:
   a. providing a competency test to a user, the competency test assessing the user's knowledge of features of health care benefits programs; and
   b. providing tutorials concerning features of health care benefits programs to the user in dependence on a score determined from the user's competency test.

5. A method for maintaining and maximizing health care coverage comprising the steps of:
   a. submitting patient data to a computer, the patient data relating to a patient and including demographic data, health data and financial data;
   b. applying health care benefits program coverage criteria for several health care benefits programs to the patient data within the computer, wherein the health care benefits program coverage criteria include enrollment eligibility conditions for each health care benefit program;
   c. within the computer, identifying one or more of the several health care benefits programs wherein the patient:
      (1) meets all of the health care benefits program coverage criteria for the health care benefits program, thereby identifying a health care benefits program for which the patient is currently eligible for enrollment, and/or
      (2) does not meet all of the health care benefits program coverage criteria for the health care benefits program but meets over at least 70% of the health care benefits program coverage criteria for the health care benefits program, thereby identifying a health care benefits program for which the patient is almost eligible for enrollment;
   d. entering updated patient data into a memory storage device, wherein the updated patient data is dynamically applied to the health care benefits program coverage criteria;
   e. upon or after entry of updated patient data, dynamically providing a report identifying:
      (1) any health care benefits programs for which the patient is currently eligible for enrollment, and
      (2) any health care benefits programs for which the patient is almost eligible for enrollment, and the health care benefits program coverage criteria needed by the patient to attain eligibility for enrollment;
   f. providing a change event status notification, the notification identifying potential changes in patient eligibility for enrollment for one or more of the health care benefits programs.

6. The method according to claim 5 further comprising the following steps:
   a. based upon health care benefits program existence, obtaining new health care benefits programs and new health care benefits program coverage criteria, wherein the patient data is applied to the new health care benefits programs; and
   b. based upon eligibility for enrollment, generating a new report for a patient.

7. The method according to claim 5 further comprising the following step:
   based upon all updated patient data, providing a health care benefits coverage proximity alert, wherein the proximity alert identifies potential health care benefits coverage programs for which the patient is almost eligible for enrollment.

8. The method of claim 5 further comprising the following step:

based upon all updated patient data, providing a health care benefits coverage proximity alert, wherein the proximity alert identifies potential loss of existing health care coverage.

9. The method of claim 5 further comprising the following step:

recording interactions between a first advocate and the patient, wherein the interaction recordation enhances advocacy for the patient when interacting with a second advocate.

10. The method of claim 5 further including the steps of:

a. calculating a probability of receiving enrollment verification;
b. identifying:
   (1) a first health care benefits program as having the greatest probability of the patient's enrollment;
   (2) a second health care benefits program as having a lower probability of the patient's enrollment than the first health care benefits program,
   (3) a third health care benefits program as having a lower probability of the patient's enrollment than the first and second health care benefits programs,
wherein at least the first and second health care benefits programs are reported in ranked order.

11. The method of claim 5 further comprising the following steps:

a. providing a competency test to a user, the competency test assessing the user's knowledge of features of health care benefits programs; and
b. providing tutorials concerning features of health care benefits programs to the user in dependence on a score determined from the user's competency test.

12. A system for identifying and maintaining consumer health care benefits including:

a. a database containing program data for health care benefits programs, the program data including health care benefits program enrollment eligibility criteria for participation in the health care benefits programs;
b. a memory storage device storing a consumer's health care related data, including demographic data, health data, and financial data;
c. a computer processor in communication with the database and memory storage device, wherein the computer processor is configured to:
   (1) apply the health care benefits program enrollment eligibility criteria to the consumer's health care related data, and
   (2) generate reports therefrom, the reports indicating:
      (a) the consumer's:
         i. current eligibility for enrollment in one or more of the health care benefits programs based on the consumer's health care related data, and
         ii. future eligibility for enrollment in one or more of the health care benefits programs based on the consumer's health care related data,
      (b) one or more of the health care benefits programs for which the consumer:
         i. is currently ineligible for enrollment, but
         ii. meets over at least 70% of the health care benefits program enrollment eligibility criteria for the health care benefits programs, and
         iii. would attain eligibility for enrollment with one or more changes in the consumer's health care related data.

13. The system according to claim 12 wherein the reports generated by the computer processor are generated whenever a change occurs in the consumer's health care related data.

14. The system according to claim 12 wherein the reports generated by the computer processor are periodically generated at a predefined frequency.

15. The system according to claim 12 wherein the reports indicating the one or more of the health care benefits programs for which the consumer is currently ineligible for enrollment include an indication of the changes needed in the consumer's health care related data to attain eligibility for enrollment.

16. The system according to claim 12 wherein the reports indicating the one or more of the health care benefits programs for which the consumer is currently ineligible for enrollment include a report of first and second health care benefits programs for which the consumer is currently ineligible for enrollment, wherein:

a. the first health care benefits program requires fewer changes in the consumer's health care related data to attain eligibility for enrollment than the second health care benefits program, and
b. the changes in the consumer's health care related data needed to attain eligibility for enrollment are reported for each of the first and second health care benefits programs.

17. The system according to claim 12 wherein the reports indicating the consumer's future eligibility for enrollment in one or more of the health care benefits programs include an indication of consumer submissions to the health care benefits programs that affect eligibility for enrollment.

18. The system of claim 12 wherein the reports further indicate, for the one or more health care benefits programs for which the consumer is currently ineligible, the changes in the consumer's health care related data that must be made in order for the consumer to attain eligibility for enrollment.

19. The system of claim 12 wherein the one or more health care benefits programs for which the consumer is currently ineligible include:

a. a first health care benefits program having the greatest probability of the consumer's enrollment;
b. a second health care benefits program having a lower probability of the consumer's enrollment than the first health care benefits program,
c. a third health care benefits program having a lower probability of the consumer's enrollment than the first and second health care benefits programs,
wherein at least the first and second health care benefits programs are provided in ranked order in the generated reports.

20. The system of claim 12 wherein the computer processor is further configured to:

a. provide a competency test to a user, the competency test assessing the user's knowledge of features of health care benefits programs; and
b. provide tutorials concerning features of health care benefits programs to the user in dependence on a score determined from the user's competency test.

21. A method for obtaining and maintaining consumer health care benefits including the following steps:

a. providing a consumer's health care related data to a computer, wherein:
   (1) the consumer's health care related data include demographic data, health data, and financial data;

(2) the computer has program data for several health care benefits programs, the program data including health care benefits program enrollment eligibility criteria for participation in the several health care benefits programs;

b. providing an initial report to the consumer from the computer, the initial report:
   (1) being based on a comparison between the consumer's health care related data and the health care benefits program enrollment eligibility criteria; and
   (2) indicating:
      (a) one or more of the several health care benefits programs in which the consumer meets all of the health care benefits program enrollment eligibility criteria for the health care benefits program, thereby indicating health care benefits programs for which the consumer is currently eligible to enroll;
      (b) one or more of the several health care benefits programs in which the consumer does not meet all of the health care benefits program enrollment eligibility criteria for the health care benefits programs but meets over at least 70% of the health care benefits program enrollment eligibility criteria for the health care benefits programs, thereby indicating health care benefits programs for which the consumer is almost eligible to enroll;

c. providing updated reports to the consumer from the computer, the updated reports:
   (1) each being provided later in time than a prior initial or updated report, and
   (2) indicating the consumer's current eligibility for enrollment in one or more of the several health care benefits programs other than those indicated as currently eligible for consumer enrollment in the initial report.

22. The method of claim 21 further including the step of providing computer-assisted enrollment to the consumer for one or more of the several health care benefits programs.

23. The method of claim 21 further including the steps of:
a. periodically updating the consumer's health care related data;
b. periodically updating the health care benefits program enrollment eligibility criteria;
c. providing updated reports to the consumer when:
   (1) the consumer's updated health care related data differ from the consumer's previously-provided health care related data, or
   (2) the updated health care benefits program enrollment eligibility criteria differ from previous health care benefits program enrollment eligibility criteria.

24. The method of claim 21 wherein the step of indicating health care benefits programs for which the consumer is almost eligible to enroll includes indicating the health care benefits program enrollment eligibility criteria that need to be met by the consumer to attain eligibility for enrollment.

25. The method of claim 21:
a. further including the step of calculating a probability of receiving enrollment verification;
b. wherein the reports provided to the consumer indicate:
   (1) a first health care benefits program as having the greatest probability of the consumer's enrollment, and
   (2) a second health care benefits program as having a lower probability of the consumer's enrollment than the first health care benefits program,
wherein the consumer is either:
   i. currently eligible to enroll in, or
   ii. almost eligible to enroll in, each of the first and second health care benefits programs.

26. The method of claim 21 further comprising the following steps:
a. providing a competency test to a user, the competency test assessing the user's knowledge of features of health care benefits programs; and
b. providing tutorials concerning features of health care benefits programs to the user in dependence on a score determined from the user's competency test.

* * * * *